United States Patent
McMahon et al.

(10) Patent No.: US 10,206,963 B2
(45) Date of Patent: Feb. 19, 2019

(54) TOPICAL MEDICINAL GEL

(71) Applicants: Joan McMahon, Midland, MI (US); Stephanie House, Merrill, MI (US)

(72) Inventors: Joan McMahon, Midland, MI (US); Stephanie House, Merrill, MI (US)

( * ) Notice: Subject to any disclaimer, the term of this patent is extended or adjusted under 35 U.S.C. 154(b) by 0 days.

(21) Appl. No.: 15/849,837

(22) Filed: Dec. 21, 2017

(65) Prior Publication Data
US 2018/0185426 A1    Jul. 5, 2018

Related U.S. Application Data

(60) Provisional application No. 62/440,023, filed on Dec. 29, 2016.

(51) Int. Cl.
*A61K 36/185* (2006.01)
*A61K 47/10* (2017.01)
*A61K 47/34* (2017.01)
*A61K 9/00* (2006.01)

(52) U.S. Cl.
CPC .......... *A61K 36/185* (2013.01); *A61K 9/0014* (2013.01); *A61K 47/10* (2013.01); *A61K 47/34* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 5,654,362 A | 8/1997 | Schutz et al. | |
| 2013/0184354 A1* | 7/2013 | Jackson | A61K 47/36 514/729 |

* cited by examiner

*Primary Examiner* — Michael Barker

(57) ABSTRACT

A novel process for incorporating cannabis extract in an emollient carrier. The carrier is a hydrophobic gel that helps to keep skin soft, smooth and hydrated.

2 Claims, No Drawings

TOPICAL MEDICINAL GEL

This application is a utility application claiming priority from U.S. provisional patent application Ser. No. 62/440,023, filed Dec. 29, 2016.

BACKGROUND OF THE INVENTION

The instant invention relates to a novel formulation incorporating cannabis extract for the purpose of alleviating pain and certain neural disorders. The carrier is a hydrophobic gel that helps to keep skin soft, smooth and hydrated.

With the discovery of the Endogenous Cannabinoid System and the legalization of Medicinal Marijuana in several states in the United States, a vast amount of studies have been done to show the efficacy of marijuana in the therapeutic treatment of disease. The cannabis extract is not soluble in water, and is often formulated using greasy oils such as olive oil or coconut oil as carriers. This formulation uses a silicone fluid as the carrier for a soft, less greasy topical.

THE INVENTION

What is claimed and disclosed herein is a process for providing a topical medicinal gel composition, the process comprising: providing cannabis extract having a predetermined concentration of cannabinoids and heating said extract to not more than 150° C. to decarboxylate the extract. Thereafter, heating the decarboxylated extract to 50° C. and combining the decarboxylated extract with glycerin and a polydimethylsiloxane having a viscosity not greater than 5000 cSt at room temperature in a 1:1:1 ratio. Thereafter, combining the mixture of decarboxylated extract, polydimethyl siloxane and glycerin with decamethylcyclopentasiloxane:dimethicone crosspolymer in predetermined ratios.

Also contemplated within the scope of this invention is a composition of matter manufactured by said process.

The process for providing cannabis extract is well-known and does not need much detail to be included herein. Once the desired dose mg/g of topical gel is determined, the extract is heated to not greater than about 150° C. to decarboxylate the resin.

Decarboxylation is a chemical reaction that removes a carboxy group and releases carbon dioxide. The term "decarboxylation" literally means removal of the COOH group and its replacement with a proton. Decarboxylation is one of the oldest organic reactions, since it often entails simple pyrolysis, and volatile products distilled from the reactor. Heating is required because the reaction is less favorable at low temperatures. Upon heating, $\Delta 9$-Tetrahydrocannabionolic acid decarboxylates to give the psychoactive compound $\Delta 9$-Tetrahydrocannabinol.

The resulting resin is then heated to approximately 50° C. A mixture of 1:1:1 of the resin:glycerin:polydimethylsiloxane is then made. If desired, a small amount of 3-(3-hydroxypropylheptamethyl-trisiloxane) ethoxylated, hydroxy-terminated (<1%) may be added to aid emulsification. This mixture is then added to Decamethylcyclopentasiloxane:dimethicone crosspolymer in a ratio of approximately 55:45 although, ratios ranging from about 35:65 to about 65:35 can be used. The ratio may be adjusted to the desired viscosity of the end product. Excipients may be added to the composition, such as essential oils, for the purpose of aiding absorption in the skin.

Information regarding the crosspolymer can be found in U.S. Pat. No. 5,654,362 that issued to Schutz, et al. on Aug. 5, 1997, which is incorporated herein in its entirety to teach the preparation of the crosspolymer.

EXAMPLES

Example 1

Cannabis extract and coconut oil have both been identified as effective sunscreens. There are a number of natural compounds that block UV rays, as they need to protect themselves from the sun as well. Cannabis has an SPF of about 6, which may be too weak on its own to serve as a sunscreen, but when combined with other natural compounds such as coconut oil, that help block UV rays, one has a nontoxic sunscreen emulsion. A sunscreen emulsion was developed, incorporating cannabis and coconut oil.

Part A Water Phase

| Ingredient | amount in parts |
| --- | --- |
| Water | 75.9 |
| Methocel ® | 0.5 |
| Benzalkoniumchloride | 0.5 |

Water was mixed with the Methocel, then adjusted in pH with 10N NaOH to a pH>10, then the BAC was added and mixed for about 30 minutes. The mixture was then heated to 50° C.

Part B Oil Phase

| | |
| --- | --- |
| Cannabis oil | 4.1 (based on actives) |
| Apricot Kernel Oil | 5.6 |
| Coconut oil | 2.8 |
| Emulsifying wax | 5.6 |
| Sunscreen ($TiO_2$ or $ZnO_2$) | |

The oil phase was heated to 70° C. for 60 minutes and the water phase to about 50° C. and the water phase was gradually added to the oil phase with continuous agitation. The material was mixed until the emulsion was uniform.

What is claimed is:

1. A process for providing a topical medicinal gel composition, said process comprising:
   a. providing cannabis extract having a predetermined concentration of cannabinoids;
   b. heating said extract to not more than 150° C. to decarboxylate the extract;
   c. thereafter, heating said decarboxylated extract to 50° C. and, combining said decarboxylated extract with glycerin and a polydimethylsiloxane having a viscosity not greater than 5000 cSt at room temperature, in a 1:1:1 ratio;
   d. combining the mixture in c. with Decamethylcyclopenta-siloxane:dimethicone crosspolymer in a ratio of 35:65 to 65:35.

2. A composition of matter manufactured by the process as claimed in claim 1.

* * * * *